United States Patent [19]

Peat

[11] Patent Number: 4,628,052
[45] Date of Patent: Dec. 9, 1986

[54] PHARMACEUTICAL COMPOSITIONS CONTAINING DEHYDROEPIANDROSTERONE AND OTHER ANESTHETIC STEROIDS IN THE TREATMENT OF ARTHRITIS AND OTHER JOINT DISABILITIES

[76] Inventor: Raymond F. Peat, P.O. Box 3427, Eugene, Oreg. 97403

[21] Appl. No.: 738,482

[22] Filed: May 28, 1985

[51] Int. Cl.$^4$ .............................................. A61K 31/56
[52] U.S. Cl. .................................................. 514/171
[58] Field of Search ........................................ 514/171

[56] References Cited

U.S. PATENT DOCUMENTS

| | | | |
|---|---|---|---|
| 4,150,128 | 4/1979 | Jasionowski | 514/171 |
| 4,224,319 | 9/1980 | Marcadet | 514/171 |
| 4,312,866 | 1/1982 | Caruso et al. | 424/244 |
| 4,315,028 | 2/1982 | Scheinberg | 424/290 |
| 4,322,405 | 3/1982 | Schulthess et al. | 424/93 |
| 4,337,334 | 6/1982 | Jensen et al. | 424/322 |
| 4,344,946 | 8/1982 | Cullen et al. | 424/250 |
| 4,355,029 | 10/1982 | Ridolfo | 424/232 |
| 4,375,468 | 3/1983 | Dunn | 424/230 |
| 4,387,093 | 6/1983 | Lysaght | 424/131 |
| 4,397,858 | 8/1983 | Welter et al. | 424/270 |
| 4,402,965 | 9/1983 | Wyburn-Mason | 424/272 |
| 4,409,243 | 10/1983 | Lieb | 424/330 |
| 4,420,481 | 12/1983 | Okazaki et al. | 424/250 |
| 4,439,432 | 3/1984 | Peat | 514/171 |

OTHER PUBLICATIONS

Merck Index, 9th Edition (1976), published by Merck & Co. Inc., p. 1181.

*Primary Examiner*—Elbert L. Roberts
*Attorney, Agent, or Firm*—Ellen P. Winner

[57] ABSTRACT

The present invention is concerned with compositions and methods of treating rheumatoid arthritis, osteoarthritis, and arthritis associated with psoriasis and with lupus and other auto-immune diseases, and also for treating non-specific joint pain associated with stress or incidental to another ailment, using dehydroepiandrosterone and/or other anesthetic steroids dissolved in an oily vehicle, and preferably administered topically or orally.

15 Claims, No Drawings

PHARMACEUTICAL COMPOSITIONS CONTAINING DEHYDROEPIANDROSTERONE AND OTHER ANESTHETIC STEROIDS IN THE TREATMENT OF ARTHRITIS AND OTHER JOINT DISABILITIES

BACKGROUND OF THE INVENTION

This invention is concerned with compositions and methods of treating rheumatoid arthritis, osteo-arthritis, and arthritis associated with psoriasis and with lupus and other auto-immune diseases, and also for treating non-specific joint pain associated with stress or incidental to another ailment, using dehydroepiandrosterone (DHEA) and/or other anesthetic steroids dissolved in an oily vehicle, and preferably administered topically or orally.

The extensive use of cortisone and related anti-inflammatory steroids in treating arthritis has been limited by the knowledge of several side effects, including calcium loss and osteoporosis, immune suppression, and atrophy of various tissues, including the adrenal glands. Nonsteroidal anti-inflammatory agents have been used with some success to avoid the glucocorticoids' side effects, but generally are ineffective in preventing the advance of the disease process. Other agents have been used or proposed which retard the advance of the disease, possibly by inhibiting mitosis, but they generally have toxic side effects.

It would be desirable to use in treatment substances which are normally present in the body at high levels, since these normal substances, especially when used in physiological quantities, rarely have harmful side effects.

The improvement which sometimes occurs during pregnancy in women suffering from arthritis has led to the experimental use of some of the hormones of pregnancy in treating arthritis, but the female sex hormones would obviously produce side effects when used in large doses in males.

Some steroidal substances, however, lack conventional hormonal activity and are normally present in significant amounts in both males and females. A number of such steroids, e.g. dehydroepiandrosterone, are present in elevated quantities during pregnancy. Such steroids have received little attention since they have been considered to be only chemical intermediates or end products destined for nothing more important than to be excreted. It was therefore surprising to find that a number of these substances are useful in the treatment of arthritis and related diseases.

It is an object of this invention to provide an anti-inflammatory pharmaceutical preparation useful for the treatment of arthritis and lacking undesirable hormonal side effects. It is a further object of this invention to provide such a pharmaceutical preparation in a form suitable for administration locally to the affected joints without requiring injection.

SUMMARY OF THE INVENTION

The present invention is concerned with compositions and methods of treating rheumatoid arthritis, osteo-arthritis, and arthritis associated with psoriasis and with lupus and other auto-immune diseases, and also for treating non-specific joint pain associated with stress or incidental to another ailment, using dehydroepiandrosterone and/or other anesthetic steroids dissolved in an oily vehicle, and preferably administered topically or orally.

DETAILED DESCRIPTION OF THE PREFERRED EMBODIMENTS

Arthritis, including rheumatoid arthritis, osteo-arthritis and arthritis associated with psoriasis and with lupus, as well as other auto-immune diseases, and non-specific joint pain associated with stress or incidental to another ailment, may be successfully treated by administering to a subject in need of such treatment, including a human patient, an effective amount of an anesthetic steroid, preferably a natural anesthetic steroid having 19 or 21 carbons, more preferably selected from compounds of the formula:

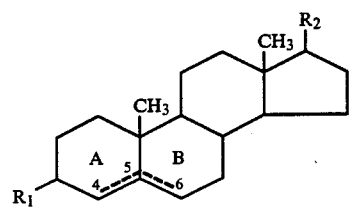

wherein $R_1$ is O or OH and $R_2$ is O, OH, or $COCH_3$; and which may contain one double bond in ring A and/or ring B.

Examples of such compounds are dehydroepiandrosterone (DHEA), iso-androsterone, etiocholanolone, progesterone, and pregnenolone.

Combinations of such steroids may be used. When the patient being treated is male, combinations containing testosterone are preferably used.

Compounds considered to be equivalent to the foregoing and also falling within the scope of this invention are steroids of the above-depicted structure having H, methyl, fluorine, or chlorine substituents, as well as easily hydrolyzable esters of all the foregoing.

Suitable pharmaceutical compositions for use according to this invention comprise at least one of the above described compounds, together with suitable pharmaceutical carriers and/or diluents, preferably the carriers specified in the preferred embodiments described below. In such pharmaceutical compositions, the proportion of therapeutically active to carrier substance can vary between about 1% and about 99% by weight. The compositions can be prepared in various pharmaceutical forms, such as granules, tablets, pills, suppositories, capsules, suspensions, salves, lotions, and the like. Pharmaceutical organic or inorganic carriers and/or diluents suitable for oral and topical use can be used to make up compositions containing the therapeutically active compounds. Diluents known to the art include vegetable and animal oils and fats. Stabilizing agents, wetting and emulsifying agents, salts for varying the osmotic pressure or buffers for securing an adequate pH value, and skin penetration enhancers can be used as auxiliary agents. The compositions may further contain other therapeutically active compounds, e.g. selected from the group of drugs commonly used in the treatment of arthritis.

For oral use, the pharmaceutical composition of the invention appropriately contains from about 10% to about 100% by weight of the active material. For topical use, the composition appropriately contains from about 1% to about 15% by weight of the active material.

Generally for oral use it is preferred that the active ingredients in dry form be mixed with tocopherol to form a paste for capsuling. For topical use, solubilization in tocopherol and olive oil is preferred.

A preferred composition for oral use comprises about 10 mg of the active material, preferably DHEA, about 50 mg pregnenolone, about 5 mg. progesterone in 1200 mg tocopherol.

A preferred composition for topical use comprises 5% of the active material, preferably DHEA, 80% mixed tocopherols, and optimally up to 10% olive oil and up to 3% progesterone. Testosterone up to about 0.5% may also be added.

The dosage required may vary from about 10 mg to about 200 mg active material orally, or 400 mg to 1000 mg active material topically, and may be repeated 2 times per day.

Generally, for oral administration, a single dosage of about 10 to 50 mg of therapeutically active compound in an appropriate carrier is effective. For topical use, a preparation containing about 8% of therapeutically active compound should be spread in a single application on the skin over the painful area in an amount of between about 0.05 ml and about 0.2 ml per square inch of skin. The preparation should be thoroughly rubbed in, and the area covered to avoid rubbing away of the compound before absorption. Warmth may be applied locally to speed absorption.

The invention will be further described in the following examples which are not to be construed as limiting the invention.

EXAMPLE 1

Combined were 100 mg of micropulverized pregnenolone with 100 mg of 10% DHEA in tocopherol to form a paste which was capsuled for oral use.

EXAMPLE 2

For oral use, 100 mg. of micropulverized pregnenolone was combined with 50 mg of 10% DHEA and 50 mg of 10% progesterone to form a paste which was capsuled.

EXAMPLE 3

For topical use, a mixture containing 72% tocopherol, 20% olive oil, 5% DHEA, 2.85% progesterone, and 0.150 testosterone was prepared by stirring the steroids into the tocopherol until dissolved, then adding the olive oil.

EXAMPLE 4

The following case histories illustrate the effectiveness of the compositions of this invention in treating arthritis and joint pain:

Case 1. A 78 year old man. He was considered to have mild osteo-arthritis, mainly in his knees. For a few years he had found it increasingly difficult and painful to rise after sitting and to walk. He coated each knee and the immediately adjoining area with a solution containing 2.5% dehydroepiandrosterone and 2.5% progesterone in a solvent consisting of equal amounts of mixed tocopherols and olive oil, and remained sitting for two hours. He rose easily, walked without pain, and his knees remained comfortable without another application of the solution. A week later he applied a 3% solution of dehydroepiandrosterone to his hands, and reported elimination of pain and increased flexibility within an hour. He has remained free of symptoms for eight months with continued treatment.

Case 2. A 72 year old woman. She was considered to have mild rheumatoid arthritis which was degenerating into osteo-arthritis, with her fingers being the most seriously affected joints. A 3% solution of dehydroepiandrosterone in olive oil was applied to one index finger, and a 10% solution of progesterone in mixed tocopherols was applied to the other index finger. All of her fingers had been rigid for over a year, with the result that she was extremely disabled. Forty minutes after the dehydroepiandrosterone solution had been applied, the finger treated with the composition containing dehydroepiandrosterone could be bent enough to touch the base of her thumb, without significant pain, but none of her other fingers showed any improvement. Several days later, the dehydroepiandrosterone solution was applied to all of her fingers, with similar good results. After about 6 months, stiffness and pain returned in spite of use of DHEA, and progesterone added to the treatment caused continued improvement.

Case 3. A 60 year old woman with a long history of rheumatoid arthritis and with serious degeneration of many joints. She had undergone surgery several times, for implantation of two artificial joints and for repair of joint cartilage. She walked as little as possible, and experienced pain, inflammation and fatigue from excessive walking. She applied a solution containing 7% dehydroepiandrosterone and 3% progesterone in solvent consisting of tocopherol, 90%, and olive oil, 10%. She applied the solution several times one afternoon and the next morning to all affected joints, including hands, wrists, elbows, knees, and ankles. She experienced what she said was complete relief, and spent the next two days walking around the town sightseeing, without any of the after-effects she had previously experienced from walking.

Case 4. A 61 year old man with mild, unclassified arthritis of the thumb and fingers of his right hand, which prevented him from playing golf, but was otherwise not seriously disabling. A solution essentially identical to that used in Case 3 was rubbed into the painful joints. In less than fifteen minutes he said that all the pain was gone, even with pressure and movement.

Case 5. A 62 year old man. His knees had been stiff, painful, and inflamed for over two years, following an accidental fall onto his knees. Arthroscopic examination revealed damaged cartilage in his right knee, and surgery was recommended to restore function. The patient refused surgery, even though he walked with difficulty and had to use his left leg, which was also affected, to lift himself slowly up steps. He said he had not slept well since he had developed the arthritis, because the pain woke him repeatedly during the night, and only the use of an analgesic would allow him to go back to sleep. He coated his knees and the skin above and below the knees to a distance of about four inches from the knee, with a total of 20 milliliters of a solution essentially identical to that used in Case 3. Within 30 minutes he appeared to be able to walk more normally, and about 45 minutes after applying the solution he remarked that he believed he was able to walk more easily. He repeated the application that night before going to sleep. Around 10 o'clock the next morning he returned and laughingly demonstrated his knees by running up the stairs, and said that he had been able to sleep through the night for the first time in years, and had not taken his usual analgesic. Topical treatment was discontinued after a few days, and he remained free of symptoms while taking 60 mg of pregnenalone orally, daily.

Case 6. A 61 year old woman. Painful and stiff joints in her hands had interfered with her work as a musician, and had made it impossible to sleep through the night, since the pain woke her two or three times during the night. A solution essentially identical to that used in Case 3 was applied to the painful joints early in the evening, and a few hours later she was able to go to sleep without taking analgesic and slept through the night. She occasionally uses the same solution preventively, and has not had a recurrence of the joint pain or stiffness.

What is claimed is:

1. A method for treating arthritis and joint pain and disability, comprising administering to a patient in need of such treatment a pharmacologically effective dose of dehydroepiandrosterone.

2. A method for treating arthritis, comprising administering to a patient in need of such treatment a pharmacologically effective dose of at least one compound selected from the group of the anesthetic class of naturally occurring steroids of the formula:

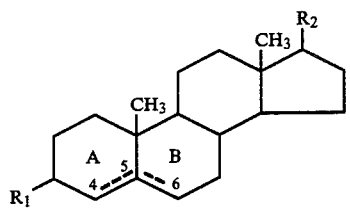

wherein $R_1$ is O or OH and $R_2$ is O, OH, or $COCH_3$; and which may contain one double bond in ring A and/or ring B.

3. The method of claim 2 in which said steroid is selected from the group consisting of: dehydroepiandrosterone, iso-androsterone, etiocholanolone, pregnenolone, and progesterone.

4. The method of claim 2 wherein the compound is administered orally.

5. The method of claim 2 wherein the compound is administered topically.

6. The method of claim 2, wherein the arthritis to be treated is osteo-arthritis.

7. The method of claim 2, wherein the arthritis to be treated is rheumatoid arthritis.

8. The method of claim 2, wherein the arthritis to be treated is arthritis associated with auto-immune disease.

9. The method of claim 2, wherein the condition to be treated comprises non-specific joint pain or joint disability resulting from stress.

10. A pharmaceutical composition useful for the treatment of arthritis comprising an effective amount of at least one compound selected from the group consisting of the formula:

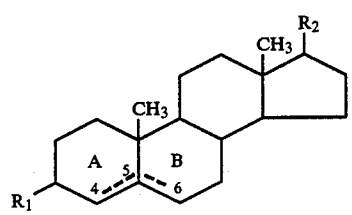

wherein $R_1$ is O or OH and $R_2$ is O, or OH; and which may contain one double bond in ring A and/or ring B and tocopherol, in a suitable pharmaceutical carrier.

11. The composition of claim 10 in which said steroid is selected from the group consisting of dehydroepiandrosterone, iso-androsterone, and etiochlolanolone, in a suitable pharmaceutical carrier.

12. The composition of claim 11 comprising an effective amount of dehydroepiandrosterone and tocopherol.

13. The composition of claim 11 also comprising progesterone.

14. The composition of claim 11 also comprising testosterone.

15. The composition of claim 11 also comprising olive oil.

* * * * *